United States Patent [19]
Cannons et al.

[11] Patent Number: 6,020,156
[45] Date of Patent: Feb. 1, 2000

[54] METHOD AND SYSTEM FOR BIOSYNTHESIZING A DESIRED BIOLOGICALLY USEFUL MACROMOLECULE IN A CHLORELLA CELL AND FOR CONTROLLING BIOSYNTHESIS THEREOF

[75] Inventors: Andrew Clive Cannons, Tampa, Fla.; Hana Nenicka Dawson, Durham, N.C.; Larry Paul Solomonson, Tampa, Fla.

[73] Assignee: University of South Florida, Tampa, Fla.

[*] Notice: This patent issued on a continued prosecution application filed under 37 CFR 1.53(d), and is subject to the twenty year patent term provisions of 35 U.S.C. 154(a)(2).

[21] Appl. No.: 08/829,613

[22] Filed: Mar. 28, 1997

Related U.S. Application Data

[60] Provisional application No. 60/014,740, Mar. 29, 1996.

[51] Int. Cl.⁷ .............................. C12P 21/02; C12N 1/13; C12N 15/11; C12N 15/79
[52] U.S. Cl. ................. 435/69.1; 435/257.3; 435/320.1; 435/471; 536/24.1
[58] Field of Search .............................. 435/320.1, 257.3, 435/471, 69.1; 536/24.1

[56] References Cited

U.S. PATENT DOCUMENTS 5,563,328  10/1996  Mitra et al. .............................. 800/294

OTHER PUBLICATIONS

Kindle et al, The Journal of Cell Biology, vol. 109 (6, Pt. 1), pp. 2589–2601, Dec. 1989.

*Primary Examiner*—Terry McKelvey
*Attorney, Agent, or Firm*—Allen, Dyer, Doppelt, Milbrath & Gilchrist, P.A.

[57] ABSTRACT

Biosynthesis of a desired macromolecule includes inserting a promoter that encodes for an endogenously produced inducible macromolecule in a Chlorella cell into a DNA vector to form a first recombinant DNA vector. A cDNA sequence that encodes for the desired macromolecule is inserted into the first recombinant DNA vector to form a second recombinant DNA vector, which is then incorporated into the microalgae cell genome to form a transformed microalgae cell. Transcription and translation of the cDNA sequence are induced in the transformed microalgae cell to biosynthesize the desired macromolecule. Control of the method is achieved with the use of a mechanism effective in repressing an expression of the endogenously produced inducible macromolecule. Then, when desired, expression of the cDNA sequence may be induced by removing the repressing agent, thereby inducing a biosynthesis of the desired macromolecule.

30 Claims, 2 Drawing Sheets

```
  1 CTGCACTGCACGTTACAGTCATTGAAGCACAATTGGGCTGCAAGCTGGAC
 51 CTCACCCGTGCATCATTCGACAGGTACTTGAGGCGTGCGCTCAAAGTCCA
101 GCCCCAGCTCCTCAATCTTTGCAGCAACCTCCTCGCTCAGTGGTGGCGAC
151 TCGTAGCCGGGGGCTTCCACCGCACGGACTGTCACCAGGCGGCGCTGCGG
201 GCTGACGGTGATGCTGTGCAGGCACGCGGCCAGTGCGGCGGCCGCCTGGG
251 GTGTTGTGGCAACTGCGGCACGCATGGCTGTGGCGGTTGGGAGGGCCTCA
301 CGCCTGCATAACGGAGGAGGAACGCAGGCGGCCACAAGATGTCAGGCCAG
351 GCTCCGAACGGTCTTGATATGATCTTGAGTAGCTCCCAAAGGTGTTTTGC
401 GCCAGGCACGGGAAGCAGCCTTCAGTGAGAGTGCGCTGCCCCAAGGGCGG
451 CGGCAGCGGCGCGGCGGCCTGTGGGTGGCTGGCCTGCCGGGCCACCCACG
501 TGCTGCAGGACTGCGAAAGTTGGCCTTGCATTGCTAACATGCACAGCAGC
551 ACTATGCGCACGAACCTGTGCCTGGCCGGCAGAGCGTAACAGGGGGGAGGG
601 TTCAGGTCTTGCTTTGGATTGTCGCACGCTTGCACAGCGCCTGATTGTCG
651 TTGTTGTTGGTTTGTAAATACGAGGGAGATCTTGCATCAGGCCTCAAAGC
701 AGCAACGCAGCTGAAATTTTTTGTGCCTTTCAGCTGAGCTCGAGACACTC
751 TCGCGAGGGTCACCTTCCTTTGGCGCAATGGCACCCCACCAGCACCTCAA
801 ATAGAGGACAGGCACGGCAGCCCTCCAATTCCACCCAGCCCTGCCAACTC
851 CTCCCTCATACTCCTCGCACCGGCCGCCATGACAGTGCTCCTGGCAGGCG
900 AGGACTCAGCCCACGGCAGCGGGTCTGCAGGAGCAGCAATG.........
```

FIG. 2.

SEQUENCE LISTING

<160> NUMBER OF SEQ ID NOS: 1

<210> SEQ ID NO 1
<211> LENGTH: 941
<212> TYPE: DNA
<213> ORGANISM: 'Axial Seamount' polynoid polychaete

<400> SEQUENCE: 1

```
ctgcactgca cgttacagtc attgaagcac aattgggctg caagctggac ctcacccgtg      60
catcattcga caggtacttg aggcgtgcgc tcaaagtcca gccccagctc ctcaatcttt     120
gcagcaacct cctcgctcag tggtggcgac tcgtagccgg gggcttccac cgcacggact     180
gtcaccaggc ggcgctgcgg gctgacggtg atgctgtgca ggcacgcggc cagtgcggcg     240
gccgcctggg gtgttgtggc aactgcggca cgcatggctg tggcggttgg gagggcctca     300
cgcctgcata acggaggagg aacgcaggcg gccacaagat gtcaggccag gctccgaacg     360
gtcttgatat gatcttgagt agctcccaaa ggtgttttgc gccaggcacg ggaagcagcc     420
ttcagtgaga gtgcgctgcc ccaagggcgg cggcagcggc gcggcggcct gtgggtggct     480
ggcctgccgg gccacccacg tgctgcagga ctgcgaaagt tggccttgca ttgctaacat     540
gcacagcagc acatgcgcac gaacctgtgc ctggccggca gagcgtaaca gggggagggg     600
ttcaggtctt gctttggatt gtcgcacgct tgcacagcgc ctgattgtcg ttgttgttgg     660
tttgtaaata cgagggagat cttgcatcag gcctcaaagc agcaacgcag ctgaaatttt     720
ttgtgccttt cagctgagct cgagacactc tcgcgagggt caccttcctt tggcgcaatg     780
gcaccccacc agcacctcaa atagaggaca ggcacggcag ccctccaatt ccacccagcc     840
ctgccaactc ctccctcata ctcctcgcac cggccgccat gacagtgctc ctggcaggcg     900
```

-continued

```
aggactcagc ccacggcagc gggtctgcag gagcagcaat g                    941
```

METHOD AND SYSTEM FOR BIOSYNTHESIZING A DESIRED BIOLOGICALLY USEFUL MACROMOLECULE IN A CHLORELLA CELL AND FOR CONTROLLING BIOSYNTHESIS THEREOF

CROSS-REFERENCE TO RELATED APPLICATION

This application claims the benefit of U.S. Provisional application Ser. No. 60/014,740, filed on Mar. 29, 1996. +gi

GOVERNMENT SUPPORT

This invention was made with U.S. Government support under grant MCB 9317557 awarded by the National Science Foundation. The government has certain rights in the invention.

FIELD OF THE INVENTION

This invention relates to methods and systems for synthesizing a biologically useful molecule in a cell. More specifically, the invention relates to methods and systems for biosynthesizing a biologically useful macromolecule in a eukaryotic cell.

BACKGROUND OF THE INVENTION

The use of prokaryotic cells to biosynthesize biologically useful macromolecules is known in the art. For example, *Escherischia coli* (*E. coli*) is routinely used to synthesize a wide variety of biological macromolecules, such as enzymes used in research, and hormones, such as insulin, used in therapeutics.

Prokaryotic synthesizers may have inherent limitations, however. For example, these cells lack some of the organelles present in eukaryotic cells, such as the endoplasmic reticulum and Golgi apparatus, which are necessary to modify proteins prior to their actual use by the organism. Such modifications include glycosylating a protein with a complex oligosaccharide en banc in the endoplasmic reticulum and then modifying the oligosaccharide in the Golgi apparatus. As a result, the biologically useful macromolecule produced by these organisms must be chemically modified prior to their use in eukaryotic organisms, such as humans.

Efforts to overcome these limitations have been made by using lower forms of eukaryotic organisms, such as yeasts, as biosynthesizers. Since these organisms are eukaryotic, they possess the organelles necessary to modify biosynthesized macromolecules such as proteins. However, these efforts have met with only limited success. For example, the lower forms of eukaryotic organisms, including yeasts, do not make all the modifications necessary to permit the use of the desired macromolecule in the intended eukaryotic organism. Thus further chemical modifications still remain to be performed prior to their intended use.

SUMMARY OF THE INVENTION

It is therefore an object of the present invention to provide a method and system for biosynthesizing a desired macromolecule.

It is a further object to provide such a method and system that utilize a eukaryotic cell as the biosynthetic agent.

It is an additional object to provide such a method and system that result in a macromolecule in need of no further modification prior to its intended use.

It is another object to provide a method and system for controlling such a biosynthetic method.

These and other objects are attained by the method and system of the present invention. The method, which is for biosynthesizing a desired macromolecule, comprises the steps of inserting a promoter of a nucleic acid sequence that encodes for an endogenously produced macromolecule in a eukaryotic microalgae cell into a DNA vector to form a first recombinant DNA vector. It is proposed that the use of a eukaryotic microalga as a bioreactor for the desired synthesis will overcome the problems associated with bacteria and yeasts. Another type of microalga that is potentially useful as a bioreactor, which also would not suffer from the limitations observed in bacteria and yeast, are Chlamydomonas cells, which form a large genus of microalgae. More than 600 species have been described worldwide from marine and freshwaters, soil, and even snow.

In a particular embodiment, the microalgae cell comprises a Chlorella cell, such as *Chlorella vulgaris* or *Chlorella sorokiniana*, which is advantageous because it, along with others of these types of organisms, grows at room temperature in a minimal medium with carbon dioxide and light. Chlorella can be easily mass cultured, manipulated, and maintained, and performs the alterations necessary to the biosynthesized macromolecule for direct use in a target organism, such as a human.

Following the promoter insertion, a cDNA sequence that encodes for the desired macromolecule is inserted into the first recombinant DNA vector at a location 3' of the promoter. This insertion forms a second recombinant DNA vector, which is then incorporated into the microalgae cell genome to form a transformed eukaryotic microalgae cell.

Finally, transcription and translation of the cDNA sequence is induced in the transfected microalgae cell, which induces a biosynthesis of the desired macromolecule.

In a preferred embodiment, the transformed cell is selected out and cloned to produce a plurality of copies, all of which are induced to biosynthesize the desired macromolecule for subsequent harvesting.

In another embodiment, the first recombinant DNA vector is provided as a starting point, and the remaining steps proceed generally as above.

In yet a further embodiment, a method for controlling the biosynthesis is provided in these types of organisms, in which repression of the expression of the cDNA sequence in the transfected microalgae cell may be achieved with the use of a mechanism effective in repressing an expression of the endogenously produced macromolecule. Then, when desired, expression of the cDNA sequence may be induced in the transformed microalgae cell by removing the repressing agent, thereby inducing a biosynthesis of the desired macromolecule.

BRIEF DESCRIPTION OF THE DRAWING

FIG. 2 lists the nucleotide sequence (SEQ ID NO:1) of the promoter region of the gene encoding for nitrate reductase in a *Chlorella vulgaris* cell.

DETAILED DESCRIPTION OF THE PREFERRED EMBODIMENTS

Figure 1:
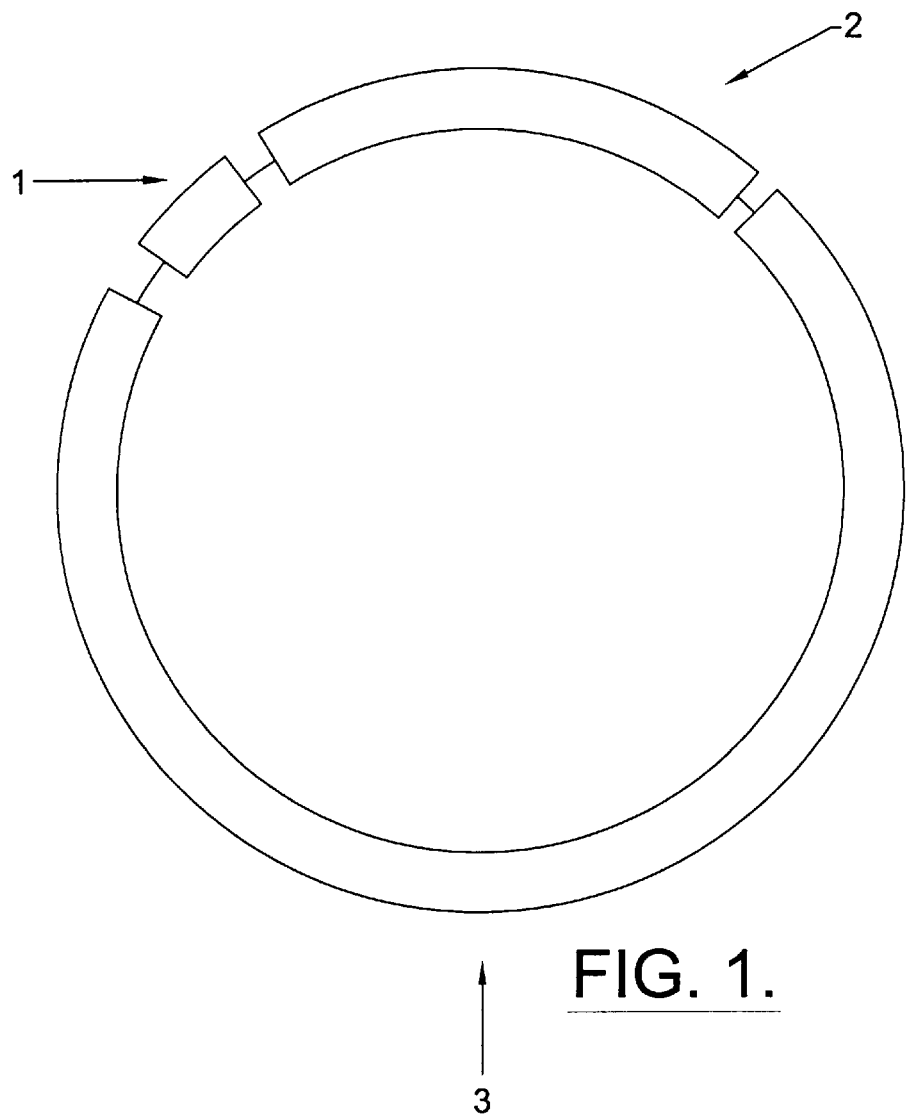
FIG. 1 is a schematic illustration of the recombinant DNA molecule.

A description of the preferred embodiments of the present invention will now be presented with reference to FIGS. 1 and 2.

In a preferred embodiment of the method and system of the present invention, the DNA vector comprises a pUC19 circular plasmid, which contains a multiple cloning site nucleic acid sequence, an origin of replication nucleic acid sequence, and an ampicillin-resistance gene. However, since ampicillin has no effect on Chlorella cells, a gene that provides resistance to G418, which can affect Chlorella cells, is incorporated into the DNA vector.

Preferably the promoter for the nitrate reductase (NR) gene is amplified via polymerase chain reaction (PCR) with primers that contain a restriction site for a particular restriction nuclease. After the amplification, the copies are incubated with the particular restriction enzyme in order to form cohesive or "sticky" ends at the 5' and 3' ends of the promoter for the NR gene.

The DNA vector is then cleaved with the same restriction endonuclease 5' of its multiple cloning site sequence. This opens the DNA vector, leaving cohesive or "sticky" ends at the 5' and 3' ends that are complementary to the cohesive ends on the promoter for the NR gene. These two nucleic acid sequences are incubated together in the presence of DNA ligase so that the promoter for the NR gene is incorporated into the DNA vector, and the DNA vector reseals itself, forming a first recombinant DNA vector. It is believed that any restriction endonuclease known in the art may be used, so long as the primers are engineered to contain the appropriate restriction site for the restriction endonuclease used and that the DNA vector contain a restriction for the restriction endonuclease 5' of its multiple cloning site sequence.

FIG. 1 schematically illustrates the second recombinant DNA vector 3, which is produced by inserting a nucleic acid molecule 2 that encodes for the biologically useful macromolecule desired to be biosynthesized in the Chlorella cell into the first recombinant DNA vector in a position 3' from the NR promoter 1 with DNA ligase. In the preferred embodiment, the nucleic acid molecule 2 comprises the cDNA of the desired macromolecule, such as, for example, insulin. The cDNA sequences for many desired biologically useful macromolecules are known in the art and could be used in the present invention.

The second recombinant DNA vector 3 is then introduced into a *Chlorella vulgaris* cell with the use of microprojectile bombardment, preferably with the use of tungsten beads as the projectiles. The beads are prepared by vortexing vigorously with 100% ethanol and soaking them in the ethanol for 15 min at room temperature. The beads are then pelleted by centrifugation at 15,000 rpm for 15 min, and the ethanol is decanted. The beads are then washed three times with sterile distilled water by vortexing and centrifugation. The final pellets are resuspended in 1 ml of 50% glycerol and then either used or stored at room temperature for up to 1–2 weeks.

The beads are then coated with the second recombinant DNA vector 3. The beads are resuspended by vortexing, and 40 µl of them are transferred to a sterile microcentrifuge tube. Approximately 2 µg of the second recombinant DNA vector is added to the tube and vortexed. With the bead mix on the bottom of the tube, 20 µl of spermidine (1 M) and 50 µl of $CaCl_2$ (2.5 M) are dotted onto the upper half of the tube, which is then centrifuged for 5–10 sec. The supernatant is removed, and 200 µl 100% ethanol is added to the tube and mixed to resuspend the pellets.

The beads are again pelleted in a microfuge, the supernatant removed, and 60 µl 100% ethanol added. The tungsten beads should now be coated with the second recombinant DNA vector.

In a preferred embodiment of the invention, a PDS-1000/He Biolistic Particle Delivery system (Bio-Rad) can be used to bombard the *Chlorella vulgaris* cells with the coated beads. All rupture disks, microcarriers, and screens should be sterilized either by autoclaving or rinsing with 100% ethanol prior to use. This system uses helium gas to force the coated tungsten beads into the Chlorella cells at a defined pressure. Preferably rupture disks of 1100 psi are used to determine the pressure at which the coated tungsten beads are shot into the Chlorella cells.

Prior to the shooting, the coated tungsten beads are suspended by flicking and sonication, and 4 µl of this mixture is spread evenly over a sterile macrocarrier, which is then allowed to air dry. The macrocarrier is then inserted into the launch assembly, which is placed into the PDS-1000/He system.

The *Chlorella vulgaris* cells are grown up to log phase and plated onto solid agar medium containing $NH_4^+$ as the nitrogen source. The density of cells is preferably approximately $3 \times 10^3$ per Petri dish. An optimal cell transformation rate has been achieved by placing the dish on the dish holder approximately 15 cm from the macrocarrier.

The system having been assembled with the installation of the Petri dish containing the cells, a vacuum of approximately 28 mm Hg is maintained and the coated bead/macrocarrier assembly blasted with helium at 1100 psi for approximately 1–2 sec. The bombarded cells are incubated on the bombarding medium at 25° C. with $CO_2$ for 12 h to recover from the bombardment.

Following recovery, the cells are scraped off the Petri dish and replated onto selection medium containing the antibiotic. The transformed cells are then selected and separated out by incubating all the cells at 25° C. with $CO_2$ for 4–6 days, after which only those colonies representing stable transformed *Chlorella vulgaris* cells and a plurality of copies of such cells will grow, as these are the cells that survive exposure to the antibiotic.

Confirmation of the transformation is achieved with the use of Southern blotting. Those colonies demonstrating successful transformation are grown up under optimal conditions for light and $CO_2$ for approximately 2 days in an ammonium-containing medium to repress the biosynthesis of the desired macromolecule.

When the growth has reached a density of approximately $10^9$ cells/ml, the cells are centrifuged at 5000 rpm. The supernatant is discarded and the cell pellet washed with sterile water, repelleted, and resuspended in medium containing nitrate as the essentially sole nitrogen source. The cells are then grown an additional 6–8 h, during which time biosynthesis of the desired macromolecule is occurring.

The desired macromolecule is harvested by washing the cells in water and resuspending in a 50 mM phosphate buffer containing a protease inhibitor (leupeptin, PMSF) at a ratio of approximately 1 g/ml. The resuspended cells are ruptured by mechanical breakage using a French pressure cell at 12,000 psi, and the lysate is collected and clarified by centrifugation.

The supernatant is then analyzed for the presence of the desired macromolecule with the use of an enzyme assay, ELISA, Western blotting (if antibody is available), or biological activity.

The system can be increased to a larger scale by growing the transformed cell and its copies in 10–20 liter fermentors under optimal conditions. After reaching the desired density, the cells can be harvested by continual action centrifugation, allowing for large volumes of cells to be pelleted by continually feeding the culture directly into the rotor.

Pelleted cells are washed and resuspended in medium containing nitrate, grown for a further 6–8 h to permit biosynthesis to proceed, and ruptured as above. The cell debris is removed, and the lysate purified for the desired macromolecule.

Another embodiment of the present invention is a method and system for controlling the biosynthesis of the desired macromolecule. This control is achieved by ligating the Chlorella promoter region of the chosen endogenously produced macromolecule, such as nitrate reductase, to the point of initial transcription of the nucleic acid sequence encoding for the desired macromolecule to form the recombinant DNA molecule. The nucleic acid sequence of this promoter region consists essentially of that set forth in SEQ ID NO:1 in the Sequence Listing of FIG. 2.

Nitrate reductase (NR; EC.1.6.6.1) is an enzyme that catalyzes the first rate-limiting step in the pathway that converts nitrate to nitrite, followed by a reduction of nitrite to ammonia. Nitrate and ammonia (or a product of ammonia) have a role in regulating NR synthesis, with nitrate acting as an inducer and ammonia as a repressor. In Chlorella, however, NR expression does not require nitrate, but rather occurs upon the removal of the repressor, ammonia, in the presence of which no NR mRNA, protein, or activity is detectable.

Although posttranscriptional controls affect the activity of NR in Chlorella, transcriptional regulation by the nitrogen source appears to be the primary mode that determines the expression of this enzyme. Consequently, the regulation of the expression of the NR gene can readily be used to control the biosynthesis of a macromolecule in a *Chlorella vulgaris* cell.

Thus, in the present invention, once the Chlorella cell has been transformed, the expression of the desired macromolecule can be repressed with the same mechanism that represses the expression of NR in the cell, namely, in this embodiment, the presence of ammonia.

When expression is desired, ammonia is removed from the cell's environs, and the desired macromolecule is biosynthesized.

Many other variations and modifications of the present invention will be apparent to those skilled in the art without departing from the spirit and scope of the present invention. The above-described embodiments are, therefore, intended to be merely exemplary, and all such variations and modifications are intended to be included within the scope of the present invention.

Having now described the invention, the operation and use of preferred embodiments thereof, and the advantageous new and useful results obtained thereby, the new and useful constructions, and reasonable equivalents thereof obvious to those skilled in the art, are set forth in the appended claims.

What is claimed is:

1. A method for biosynthesizing a desired macromolecule in a microalgae cell comprising the steps of:
   inserting an isolated promoter into a DNA vector to form a first recombinant DNA vector, the promoter comprising the sequence set forth as SEQ ID NO:1;
   inserting a cDNA sequence that encodes the desired macromolecule into the first recombinant DNA vector 3' of the promoter to form a second recombinant DNA vector;
   incorporating the second recombinant DNA vector into the genome of the microalgae cell to form a transformed microalgae cell; and
   inducing transcription and translation of the cDNA sequence in the transformed microalgae cell, thereby inducing a biosynthesis of the desired macromolecule.

2. The method recited in claim 1, further comprising the step, following the incorporating step, of cloning the transformed microalgae cell to produce a plurality of copies thereof, and wherein the inducing step further comprises inducing transcription and translation of the cDNA sequences in the copies.

3. The method recited in claim 1, further comprising the step, following the inducing step, of harvesting the desired macromolecule.

4. The method recited in claim 1, wherein the microalgae cell comprises a Chlorella cell.

5. The method recited in claim 4, wherein the Chlorella cell is selected from the group consisting of *Chlorella vulgaris* and *Chlorella sorokiniana*.

6. The method recited in claim 1, wherein the promoter inserting step comprises inserting the isolated promoter into a circular plasmid having:
   a multiple cloning sequence;
   an origin of replication sequence located 5' to the multiple cloning sequence; and
   an antibiotic-resistance gene sequence located 5' to the origin of replication sequence and 3' to the multiple cloning sequence, the antibiotic-resistance gene sequence encoding a macromolecule that confers antibiotic resistance to the transformed microalgae cell.

7. The method recited in claim 6, wherein the promoter inserting step further comprises the steps of:
   forming a recombinant promoter containing the isolated promoter and restriction sites for a restriction endonuclease at the 5' end and the 3' end of the isolated promoter;
   cleaving the recombinant promoter at the 5' end and the 3' end thereof with the restriction endonuclease;
   cleaving the DNA vector 5' of the multiple cloning sequence with the restriction endonuclease; and
   ligating the cleaved recombinant promoter and the cleaved DNA vector in the presence of DNA ligase.

8. The method recited in claim 7, wherein the forming step comprises amplifying the isolated promoter with the use of DNA primers comprising the restriction sites.

9. The method recited in claim 8, wherein the amplifying comprises performing a polymerase chain reaction.

10. The method recited in claim 7, wherein the cDNA sequence inserting step comprises:
    cleaving a nucleic acid sequence containing the cDNA sequence with a second restriction endonuclease 5' and 3' of the cDNA sequence;
    cleaving the first recombinant DNA vector with the second restriction endonuclease at the multiple cloning sequence; and
    ligating the cleaved nucleic acid sequence containing the cDNA sequence and the cleaved first recombinant DNA vector in the presence of DNA ligase.

11. The method recited in claim 10, wherein the second recombinant DNA vector incorporating step comprises bombarding the microalgae cell with a microprojectile having the second recombinant DNA vector removably attached thereto, to form said transformed microalgae cell.

12. The method recited in claim 7, further comprising the step, preceding the transcription and translation inducing step, of selecting out the transformed microalgae cell.

13. The method recited in claim 12, wherein the selecting out step comprises exposing the transformed microalgae cell to the antibiotic corresponding to the antibiotic-resistance gene.

14. The method recited in claim 1, further comprising the step of subjecting the transformed microalgae cell to nutrient conditions sufficient to grow a plurality of copies thereof.

15. The method recited in claim 14, wherein the subjecting step comprises incubating the transformed microalgae cell in nutrient conditions containing ammonia.

16. The method recited in claim 15, wherein the cDNA sequence transcription and translation inducing step comprises exposing the transformed microalgae cell to nitrate.

17. A system for biosynthesizing a desired macromolecule comprising:
    a microalgae cell;
    a DNA vector;
    an isolated promoter comprising the sequence set forth as SEQ ID NO:1, the promoter insertable into the DNA vector for forming a first recombinant DNA vector;
    a cDNA sequence that encodes the desired macromolecule which is insertable into the first recombinant DNA vector 3' of the promoter for forming a second recombinant DNA vector;
    a means for incorporating the second recombinant DNA vector into the genome of the microalgae cell; and
    a means for inducing transcription and translation of the cDNA sequence in the transformed microalgae cell, thereby inducing a biosynthesis of the desired macromolecule.

18. The system recited in claim 17, further comprising a means for cloning the transformed microalgae cell to produce a plurality of copies thereof, and a means for inducing transcription and translation of the cDNA sequence in the copies.

19. The system recited in claim 17, wherein the microalgae cell comprises a Chlorella cell.

20. The system recited in claim 19, wherein the Chlorella cell is selected from the group consisting of *Chlorella vulgaris* and *Chlorella sorokiniana*.

21. The system recited in claim 19, wherein the second recombinant DNA vector incorporating means comprises a means for bombarding the microalgae cell with a microprojectile having the second recombinant DNA vector removably attached thereto.

22. The system recited in claim 21, wherein the microprojectile comprises a tungsten bead coated with the second recombinant DNA vector.

23. A method for controlling a biosynthesis of a desired macromolecule comprising the steps of:

inserting an isolated promoter comprising the sequence set forth as SEQ ID NO:1 into a DNA vector to form a first recombinant DNA vector;

inserting a cDNA sequence that encodes the desired macromolecule into the first recombinant DNA vector 3' of the promoter to form a second recombinant DNA vector;

incorporating the second recombinant DNA vector into the genome of a microalgae cell to form a transformed microalgae cell;

when desired, inducing expression of the cDNA sequence in the transformed microalgae cell, thereby inducing said biosynthesis of the desired macromolecule; and when desired, repressing the expression of the cDNA sequence in the transformed microalgae cell with the use of a mechanism effective in repressing the expression from the promoter, thereby controlling the biosynthesis.

24. The method recited in claim 23, wherein the repressing step comprises exposing the transformed microalgae cell to ammonia.

25. An isolated promoter comprising the nucleic acid sequence as set forth in SEQ ID NO:1.

26. A recombinant DNA vector comprising a DNA vector and an isolated promoter comprising the nucleic acid sequence as set forth in SEQ ID NO:1.

27. The recombinant DNA vector recited in claim 26, further comprising a cDNA sequence that encodes a desired macromolecule positioned 3' of the promoter.

28. A transformed microalgae cell for biosynthesizing a desired macromolecule, said microalgae cell having a genome comprising a recombinant DNA vector incorporated therein, the recombinant DNA vector comprising:

a DNA vector;

an isolated promoter comprising the nucleic acid sequence as set forth in SEQ ID NO:1; and a cDNA sequence that encodes said desired macromolecule positioned 3' of the promoter.

29. The microalgae cell recited in claim 28, wherein the cell comprises a Chlorella cell.

30. The microalgae cell recited in claim 29, wherein the Chlorella cell is selected from the group consisting of *Chlorella vulgaris* and *Chlorella sorokiniana*.

* * * * *